United States Patent
Ding

(10) Patent No.: US 6,903,046 B2
(45) Date of Patent: Jun. 7, 2005

(54) METAL MODIFIED PD/NI CATALYSTS

(75) Inventor: Hao Ding, Macungie, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 10/825,027

(22) Filed: Apr. 15, 2004

(65) Prior Publication Data

US 2004/0199017 A1 Oct. 7, 2004

Related U.S. Application Data

(62) Division of application No. 10/137,053, filed on May 1, 2002, now Pat. No. 6,762,324.

(51) Int. Cl.$^7$ ........................... B01J 21/18; B01J 21/08; B01J 23/58; B01J 23/44

(52) U.S. Cl. ...................... 502/185; 502/183; 502/184; 502/244; 502/245; 502/250; 502/259; 502/262; 502/328; 502/329; 502/330; 502/332; 502/333; 502/335

(58) Field of Search ............................... 502/183–185, 502/244, 245, 250, 259, 262, 332, 328–330, 333, 335

(56) References Cited

U.S. PATENT DOCUMENTS

| | | | |
|---|---|---|---|
| 3,127,356 A | | 3/1964 | Hamilton, Jr. |
| 3,781,227 A | | 12/1973 | Sokolsky et al. |
| 3,925,490 A | * | 12/1975 | Reich et al. ................. 568/914 |
| 3,935,264 A | | 1/1976 | Bhutani |
| 4,142,962 A | * | 3/1979 | Yates et al. .................. 208/109 |
| 4,238,365 A | | 12/1980 | Antos |
| 4,743,577 A | | 5/1988 | Schroeder et al. |
| 4,792,622 A | | 12/1988 | Yokota et al. |
| 4,792,626 A | | 12/1988 | Becher et al. |
| 5,296,631 A | | 3/1994 | Abe et al. |
| 5,932,769 A | | 8/1999 | Vedage et al. |
| 5,990,344 A | * | 11/1999 | Couves et al. ............... 560/245 |
| 6,005,143 A | | 12/1999 | Machado et al. |
| 6,350,717 B1 | * | 2/2002 | Frenzel et al. ............... 502/330 |
| 6,492,299 B1 | * | 12/2002 | Couves et al. ............... 502/339 |
| 6,660,675 B2 | * | 12/2003 | Chaudhari et al. ............. 502/66 |
| 2003/0023121 A1 | * | 1/2003 | Frenzel et al. ............... 585/259 |

FOREIGN PATENT DOCUMENTS

| | | |
|---|---|---|
| EP | 1 036 784 A1 | 1/2000 |
| EP | 1 358 935 A1 | 11/2003 |
| JP | 47-91069 | 5/1974 |
| JP | 11-47597 | 2/1999 |

OTHER PUBLICATIONS

F. Boccuzzi, et al., "Surface Composition of Pd–Fe Catalysts Supported on Silica," *J. Chem. Soc.*, Faraday Trans. (1995), 91 (18), 3237–44, no month.

European Search Report 03008826.4–2104 dated Aug. 4, 2003.

* cited by examiner

*Primary Examiner*—David Sample
*Assistant Examiner*—Patricia L. Hailey
(74) *Attorney, Agent, or Firm*—Michael Leach

(57) ABSTRACT

This invention relates to improved catalytic compositions suited for use in hydrogenation processes and to an improved process for hydrogenating organic compounds as in amination of alcohols or hydrogenation of nitro groups to the amine using the catalyst. The catalytic composition is more particularly an improvement in nickel catalysts promoted with palladium carried on a support. The improvement resides in including a promoting effect of a metal M and/or its oxide, selected from Zn, Cd, Cu, and Ag, typically from about 0.01 to 10% by weight of the support.

9 Claims, No Drawings

METAL MODIFIED PD/NI CATALYSTS

CROSS-REFERENCE TO RELATED APPLICATIONS

This application is a division of U.S. Ser. No. 10/137,053 filed on May 1, 2002, now U.S. Pat. No. 6,762,324.

BACKGROUND OF THE INVENTION

Processes for the hydrogenation of organic compounds including those having functional groups have been widely practiced. Amination of alcohols, hydrogenation of nitrites to amines, hydrogenation of nitro groups as in the conversion of nitroaromatics to aromatic amines are commonplace industrial reactions. Catalysts used for the industrial hydrogenation of these compounds typically are based upon Group VIII metals. However, cobalt and nickel often are the primary metals employed. Promoter metals have been added to these catalytic metals to alter reactivity, byproduct formation and the like.

Representative patents and articles illustrating hydrogenation processes and the catalytic metals used therefor are as follows:

U.S. Pat. No. 3,127,356 discloses an improved process for preparing catalysts for the hydrogenation of organic compounds such as organic nitro compounds. Platinum, palladium or nickel is deposited on an inert support, and then, an oleophilic carbon is added to the system. Subsequently the metal is reduced to an activated state. Activating components, e.g., oxides of iron, nickel magnesium, manganese, chromium, vanadium, and tungsten may be added at various stages.

U.S. Pat. No. 4,792,626 discloses a process for the hydrogenation of dinitrotoluene to toluenediamine in the presence of a modified Raney nickel catalyst. The Raney catalyst is the product of an alkali treatment of an alloy of from 50–95 wt % aluminum and 4–45 wt % nickel or cobalt. These metals are modified with metals from the $1^{st}$, $4^{th}$, $5^{th}$, $6^{th}$, $7^{th}$ and $8^{th}$ subgroups of the periodic table. Iron, ruthenium, chromium, molybdenum, tungsten, niobium, tantalum, vanadium, titanium, copper, zirconium and hafnium are preferred. A small proportion of carbon monoxide is added to the reaction to prevent formation of N-alkyl toluenediamine.

Boccuzzi, F., Guglielminotti, E; Pinna, F., Signoretto, M.; *Surface Composition of Pd—Fe Catalysts supported on Silica*, J. Chem. Soc., Faraday Trans. (1995), 91 (18), 3237–44, disclose the formation of highly dispersed Pd—Fe bimetallic aggregates as catalysts for hydrogenation reactions.

U.S. Pat. No. 3,935,264 discloses the hydrogenation of dinitrotoluene (DNT) to toluenediamine (TDA) in the presence of an aliphatic alcohol. Preferred catalytic metals include nickel, platinum, palladium and mixtures. Raney nickel is the preferred catalytic metal. Carbon monoxide addition is found to be effective in minimizing the formation of N-alkyl toluenediamine type byproducts in the catalytic hydrogenation of DNT.

U.S. Pat. No. 6,005,143 discloses the hydrogenation of dinitrotoluene in a monolith catalytic reactor. The catalytic metal employed in the monolith catalytic reactor is a Pd/Ni bimetallic. In these catalysts, the metal loading is about 10% nickel and 1% palladium.

U.S. Pat. No. 4,743,577 discloses metallic catalysts for hydrogenation and decarbonylation reactions. The catalytic metals are based upon a porous, sintered support and a catalytic metal. Catalytic metals are dispersed upon the support in thin layers or electroplated from a salt solution. Catalyst metals are selected from among palladium, nickel, rhodium, platinum, copper, ruthenium, cobalt and mixtures.

U.S. Pat. No. 5,296,631 discloses a process for producing N-alkyl-N-methyl amines wherein a higher alcohol is reacted with methylamine. The catalyst employed is either one comprised of copper, zinc and ruthenium or one comprised of copper, zinc and palladium.

JP S47-91069 discloses the liquid phase hydrogenation of nitrites to amines using a catalyst comprised of nickel and palladium carried on an alumina support. Pd/Ni ratios range from about 0.1 to about 0.8. The proportion of primary amine is related to the level of palladium in the catalyst.

JP HEI 11-47597 discloses a hydrogenation catalyst employing a porous lithium aluminate possessing spinel as a support. A wide range of catalytic metals are suggested which include ruthenium, rhodium, silver, palladium carried on the support. Divalent metals such as magnesium zinc, cobalt nickel and copper are suggested as an additive.

Some of the problems associated with prior art palladium promoted nickel hydrogenation catalysts, i.e., Pd/Ni bimetallic catalysts, include that of relatively low selectivity and deactivation. Deactivation can be caused by a sintering of the metal and/or fouling caused by undesirable byproduct formation. Ring hydrogenated products (lights) and oligomer products (heavies) are believed to be the common byproducts causing fouling of the catalysts.

BRIEF SUMMARY OF THE INVENTION

This invention relates to improved catalytic compositions suited for use in hydrogenation processes and to an improved process for hydrogenating organic compounds as in amination of alcohols or hydrogenation of nitro groups to the amine using the catalyst. The catalytic composition is more particularly an improvement in palladium/nickel catalysts which are carried on a support. The improvement resides in including a promotingly effective amount of a metal M selected from Zn, Cd, Cu, and Ag, typically from about 0.01 to 10% by weight of the support.

Significant advantages may be achieved by the use of the catalytic compositions in hydrogenation processes and these include:

an ability to achieve high selectivity of desired product;

an ability to achieve excellent rates of reaction during hydrogenation; and, an ability to achieve excellent catalyst life partially due to minimal byproduct formation.

DETAILED DESCRIPTION OF THE INVENTION

As illustrated in the Background of the Invention, Pd/Ni as bimetallics are known and widely used as catalysts for a number of hydrogenation reactions, such as the hydrogenation of nitroaromatic compounds to aromatic amines. The hydrogenation of dinitrotoluene (DNT) to toluenediamine (TDA) and the hydrogenation of nitrites are representative.

These catalytic metals are carried on a support, whether active or not, such as alumina or silica. Other materials that may be used as supports include titania, lithium aluminate, zeolites, kiesulguhr, diatomaceous earth, carbon and so forth. Monolith substrates having from 100 to 1200 cells per inch, preferably from 400 to 800 cells per inch may be used in an embodiment of the invention. Monolith substrates may be made from carbon, cordierite, ceramics and numerous other components. Such substrates may be used to anchor the above mentioned support materials for fixed bed applications.

The active metals, i.e., Ni and Pd, for effecting the hydrogenation reactions are impregnated into or on the support by conventional methods such as incipient wetness or other methods of impregnation and deposition. In the case of monolithic catalysts, washcoat support materials, such as alumina, lithium aluminate and the like, are added to the surface of monolith substrate as catalyst support. The active metals are added and subsequently fixed to the washcoat support to form a catalyst. Typically the metals are applied to or incorporated into the support material using the metal oxides which subsequently get reduced to the active metal.

The active metals are incorporated into the support, e.g., by impregnation in various amounts. The level of nickel, as metal, incorporated into the support will range from about 10 to 25 wt %, preferably from 15 to 20 wt %; the palladium in the support will range from about 0.01 to 20 wt %, preferably from 0.5 to 1.5 wt %, and the amount of promoting metal M in the support will range from about 0.001 to 10 wt %, preferably from 0.1 to 2 wt %. Typically, the weight ratio of nickel to palladium will range from 1–100:1, preferably from 10–40:1 and the weight ratio of nickel to promoting metal M will range from about 10–1000:1, preferably from 10–200:1 and the weight ratio of palladium to metal M will range from 0.5–10:1.

The catalysts described herein are well suited for hydrogenation reactions associated with the catalytic hydrogenation of organic compounds employing palladium/nickel catalysts. Hydrogenation reactions that can be carried out using the improved catalysts include the hydrogenation of unsaturated hydrocarbons, amination of alcohols, conversion of nitro groups to amines and the hydrogenation of nitriles. Unsaturated hydrocarbons which may be hydrogenated are aromatic compounds, olefins and alkynes.

Examples of alkanols suited for amination by reaction with ammonia in the presence of hydrogen include lower $C_{1-8}$ alkanols, such as methanol, ethanol, i and n-propanol, butanol, and so forth, and cycloaliphatic alcohols, such as cyclohexanol. Nitriles which can be hydrogenated include the $C_{1-8}$ aliphatic nitrites, e.g., acetonitrile, propionitrile, butyronitrile, acrylonitrile and so forth. One of the important industrial applications for these catalysts is the hydrogenation of aromatic nitro compounds to form the aromatic amines Examples include the hydrogenation of mononitrotoluene and dinitrotoluene (DNT).

Although not intending to be bound by theory, in the case of DNT hydrogenation, the presence of Pd keeps Ni at a reduced state at effective DNT conversion temperatures Therefore, such catalysts provide good DNT hydrogenation activity to TDA. However, Pd is also active in ring hydrogenation, causing the formation of light byproducts (lights) in the process. The metals M tend to reduce the lights and byproducts formed in the hydrogenation process.

EXAMPLE 1

Modification Of Pd/Ni Bimetallic Monolith Catalyst With Zinc—Five zinc modified Pd/Ni impregnated monolith catalysts were prepared as follows. A commercial Pd/Ni monolith catalyst comprised of a cordierite monolith substrate that contained 20 wt % of alumina washcoat support having Pd in an amount of 1.0 wt % with respect to the washcoat support and Ni in an amount of 20.0 wt % with respect to the washcoat support was dipped into an aqueous solution containing 2 wt % $Zn(NO_3)_2(6H_2O)$ at room temperature. The resulting wet monolith catalyst was dried at 110° C. for 4 hours and then calcined at 380° C. for 6 hours. Different Zn loadings were achieved by changing the concentration of $Zn(NO_3)_2(6H_2O)$ in the dipping solution from 0.2 wt % to 20 wt %. Zn loadings in the five monolith catalysts resulting from zinc addition were 0.29%, 0.48%, 0.80%, 3.0%, 4.8% with respect to the weight of the washcoat support. Zinc levels were determined by Inductive Coupled Plasma (ICP).

EXAMPLE 2

Modification Of Pd/Ni Bimetallic Monolith Catalyst With Copper—The procedure of Example 1 was followed except that copper modification was achieved by utilizing a 2 wt % $Cu(NO_3)_2$ solution. 1.0% Cu with respect to the weight of the washcoat support was added.

EXAMPLE 3

Modification Of Pd/Ni Bimetallic Monolith Catalyst With Silver—Silver modification was achieved with 2 wt % $AgNO_3$ solution using the method described in Example 1. 1.0% Ag with respect to the weight of the washcoat support was added.

EXAMPLE 4

Influence Of Zn Concentration On DNT Hydrogenation Selectivity—The effectiveness of the five zinc modified Pd/Ni monolith catalysts prepared in Example 1 for performance and selectivity control in the hydrogenation of dinitrotoluene (DNT) was determined using a batch reactor.

A toluenediamine/water (TDA/water) heel was first charged to the batch reactor and the monolith catalyst placed in the reactor. The mixture was brought to reaction conditions (140° C., 600 psi $H_2$). DNT was then pumped in at four different rates (1, 2, 4, 8 g/min) for a total duration of 1 hour. The activity of the catalyst (hydrogenation rate) was recorded during this period of time. The DNT feeding was stopped after 1 hour and the TDA product mixture was kept at reaction conditions for additional 2 days, during which the selectivity of the catalyst was checked by GC through periodical sampling the reactor.

It was found that the presence of Zn in the Pd/Ni monolith catalyst effectively suppressed formation of lights and tars (byproducts) even at concentrations as low as 0.3 wt % based on support. As a generalized trend, a higher concentration of Zn in the monolith catalyst gave even better selectivity control up to around 0.8 wt %. Then the control leveled off with virtually no lights formation, and yet the activity of the catalyst was not compromised even at high Zn loading of 5 wt %. Table 1 presents data showing the DNT hydrogenation selectivity enhancement by the Zn modified catalysts.

TABLE 1

| Zn % | Lights % | Tars % |
|---|---|---|
| 0.00 | 7.50 | 1.00 |
| 0.29 | 2.90 | 2.30 |
| 0.48 | 2.20 | 1.00 |
| 0.80 | 0.30 | 0.10 |
| 3.00 | 0.29 | 0.44 |
| 4.80 | 0.19 | 0.54 |

EXAMPLE 5

Influence Of Different Metal Promoters On DNT Hydrogenation Selectivity—The procedure of Example 4 was followed to determine the effectiveness of the Cu and Ag modified monolith catalysts formed in Examples 2 and 3. The amounts of light products generated with each modified catalyst were compared against the unmodified Pd/Ni catalyst. Table 2 shows the effect of metal promoters on light products formation. The data in Table 2 demonstrates that Cu and Ag were effective promoters to suppress the formation of light products in the DNT hydrogenation process. However, their effectiveness was less than that of zinc as illustrated in Table 2.

TABLE 2

|         | Lites % | Tar % |
|---------|---------|-------|
| Pd/Ni    | 7.50    | 1.00  |
| Pd/Ni/Zn | 0.30    | 0.10  |
| Pd/Ni/Cu | 1.50    | 1.10  |
| Pd/Ni/Ag | 2.00    | 2.30  |

In summary, a Zn modified Pd/Ni catalyst resulted in overall lights formation of 0.3% in 48 h (total byproduct: <1%). This high level of selectivity was unexpected as the unmodified catalyst typically resulted in 7.5% lights (total byproduct: 9%) under the same conditions (140° C., 600 psi $H_2$). The Cu and Ag catalysts are also significantly better than the non-modified Pd/Ni catalyst but not as good or as effective in promoting selectivity as zinc.

EXAMPLE 6

Synthesis Of Ni(20%)/Pd(1%)/Zn(1%) On Alumina Support—An alumina supported catalyst containing palladium, nickel and zinc was prepared as follows. Initially 1.8 g zinc nitrate hexahydrate was dissolved in approximately 4 ml HPLC grade $H_2O$ and then 39.6 g nickel nitrate hexahydrate and 5 ml HPLC grade water were added to the zinc solution. The mixture was stirred on a hotplate. When completely dissolved, 4.9 g palladium nitrate solution (8.2% Pd) was added to the zinc/nickel solution. 31.2 g gamma alumina (heat treated Catalpal® B alumina) was then blended in until alumina was uniform in color. The mixture was transferred to a porcelain dish, dried at 110° C. in air for 1 hr and further calcined at 380° C. in air for 4 hrs.

EXAMPLE 7

Hydrogenation Of Butyronitrile Using Ni(20%)/Pd(1%)/Zn(1%) On Alumina Support—1.2 g of the catalyst of Example 6, was reduced initially by hydrogen at 500° C. and added to a 500 ml Parr reactor. Butyronitrile (80 g, 98%, Aldrich) was then charged to the reactor. The reactor was brought to a temperature of 125° C. and pressurized to 500 psig with $H_2$. The reactor was stirred at 1500 rpm. The hydrogenation reaction was stopped when hydrogen no longer was consumed. Multiple uses of the same catalyst were achieved by discharging the reaction product through a internal filter and recovering the used catlyst. The used catalyst then was recharged to the reactor and fresh feed added. The final products were analyzed by GC and the results are shown in Table 3.

TABLE 3

| Use | $T_{95(min)}$ | Conv (%) | Butylamine (%) | Dibutylamine (%) | Tributylamine (%) |
|-----|---------------|----------|----------------|------------------|-------------------|
| 1   | 196           | 99.7     | 69.3           | 28.7             | 0.5               |
| 2   | 127           | 98.3     | 64.9           | 28.2             | 0.7               |
| 3   | 125           | 99.8     | 66.2           | 30.9             | 0.8               |
| 4   | 122           | 99.8     | 67.3           | 31.6             | 0.9               |

The results show excellent conversion of the nitrile to the primary amine. Minimal amounts of tertiary amine were formed.

EXAMPLE 8

Ethanol Amination Using Ni(20%)/Pd(1%)/Zn(1%) On Alumina Support—A Ni(20%)/Pd(1%)/Zn(1%) catalyst as prepared in Example 6 was first pressed into pellets and then screened for particle size using 12 and 18 mesh screens. Approximately 10 cc of catalyst was weighed out and placed in a tube reactor. The temperature of the reactor was slowly increased to 410° C. over a 2-hour period. To reduce the catalyst metal, the catalyst was kept at this temperature under 100 psi hydrogen with a flow rate of 80 ml/min for 4 hours. Once the catalyst metal was reduced, the temperature was lowered to 185° C. and ethanol (7.0 ml/hr) was fed to the reactor along with ammonia and hydrogen ($NH_3$/ethanol/$H_2$=2/1/1.5 molar ratio). The sample stream was analyzed by GC equipped with a FID detector. The data is shown in Table 4.

TABLE 4

| Time on Stream | EtOH Conv. (%) | MEA (%) | DEA (%) | TEA (%) |
|----------------|----------------|---------|---------|---------|
| 24 hr          | 84.602         | 34.551  | 47.421  | 18.028  |
| 48 hr          | 83.550         | 34.635  | 47.716  | 17.649  |
| 72 hr          | 82.587         | 35.209  | 47.069  | 17.722  |
| 144 hr         | 82.143         | 34.479  | 47.501  | 18.020  |
| 168 hr         | 80.714         | 35.834  | 46.669  | 17.497  |

The results show excellent conversion and catalysts life were achieved using the zinc modified Pd/Ni catalyst.

I claim:

1. In a catalytic composition consisting of palladium/nickel carried on a support which is suited for use in a hydrogenation process, the improvement which resides in the inclusion of a promotingly effective amount of zinc.

2. The catalytic composition of claim 1 wherein the nickel is present in an amount from about 10 to 25 percent by weight of the support.

3. The catalytic composition of claim 2 wherein the palladium is present in an amount from 0.01 to 20 percent by weight of the support.

4. The catalytic composition of claim 3 wherein the zinc is present in an amount from about 0.001 to 10 wt % of the support.

5. The catalytic composition of claim 4 wherein the weight ratio of nickel to palladium is from 1–100:1.

6. The catalytic composition of claim 5 wherein the weight ratio of nickel to zinc is from about 10–1000:1.

7. The catalytic composition of claim 6 wherein the weight ratio of palladium to zinc is from 0.5–10:1.

8. The catalytic composition of claim 7 wherein the support is selected from the group consisting of alumina, lithium aluminate, carbon, silica, titania, zeolite, kiesulguhr or cordierite monolith with above supports as washcoat.

9. The catalytic composition of claim 8 wherein the nickel is present in an amount of from 15 to 20% by weight of the support, the palladium is present in an amount from 0.5 to 1.5% by weight and the zinc is present in an amount from 0.1 to 2% by weight.

* * * * *